United States Patent [19]

Burguette

[11] 4,180,673

[45] Dec. 25, 1979

[54] ELECTRON BEAM SENSITIVE MONOMER

[75] Inventor: Mario D. Burguette, Maplewood, Minn.

[73] Assignee: Minnesota Mining and Manufacturing Company, Saint Paul, Minn.

[21] Appl. No.: 685,118

[22] Filed: May 10, 1976

[51] Int. Cl.² .......................................... C07C 101/44
[52] U.S. Cl. ..................................... 560/26; 580/25; 580/115; 580/158; 560/185
[58] Field of Search ................... 260/484 A; 560/158, 560/26, 115

[56] References Cited

U.S. PATENT DOCUMENTS

| | | | |
|---|---|---|---|
| 2,141,546 | 12/1938 | Strain | 560/185 |
| 2,599,549 | 6/1952 | Fisher et al. | 260/484 A |
| 3,297,745 | 1/1967 | Fekete et al. | 560/26 |
| 3,458,561 | 7/1969 | Kautter et al. | 560/185 |
| 3,907,865 | 9/1975 | Miyata et al. | 560/26 |
| 3,979,426 | 9/1976 | Demajistre | 560/158 |

FOREIGN PATENT DOCUMENTS

| | | | |
|---|---|---|---|
| 1960716 | 6/1971 | Fed. Rep. of Germany | 560/185 |
| 2308036 | 10/1973 | Fed. Rep. of Germany | 560/158 |
| 2365631 | 10/1975 | Fed. Rep. of Germany | 560/158 |

*Primary Examiner*—Paul J. Killos
*Attorney, Agent, or Firm*—Cruzan Alexander; Donald M. Sell; Richard Francis

[57] ABSTRACT

Electron-beam sensitive monomers contain two to three terminal acryloxy and one intermediate divalent or trivalent hydrocarbylene group the valences of which are respectively linked in each case by at least one of acyloxylene and alkoxycarbonylamidolene units.

4 Claims, No Drawings

ELECTRON BEAM SENSITIVE MONOMER

This invention relates to monomers, polymerization of which is initiated by an electron-beam although the monomers are substantially stable to radiation in the visible and ultraviolet ranges of the spectrum.

Numerous polymerizable monomers are known which are sensitive to radiation in the visible and untraviolet range. Such monomers are often referred to as photopolymerizable. The rates at which polymerization of such monomers is brought about on exposure to light is generally not very rapid. Not infrequently, exposure for several seconds is necessary even to ultraviolet light of considerable intensity.

A source of active radiation of even greater energy than ultraviolet light is found in electron-beams which are produced by numerous commercially available apparatuses. Materials which can be polymerized using an electron-beam might be expected to be capable of rapid polymerization because energy is absorbed by the material to be polymerized more directly from the beam. Furthermore, although almost any monomer might be expected to be polymerizable by an electron-beam at least some monomers should also be relatively insensitive to radiation of light energy and hence to have better "keeping" properties and shelf-life. Because exposure to electron-beams may be accomplished in vacuum it is desirable that monomers for use with electron-beams be relatively nonvolatile.

It is a principal object of this invention to provide monomers which are rapidly polymerizable under the action of an electron-beam but are substantially unpolymerizable when exposed to visible or ultra-violet radiation even for very prolonged times. Other objects will become evident hereinelsewhere.

In accordance with the above other objects of the invention it has been found that a new class of acrylate monomers provides not only the desired polymerizability on exposure to an electron-beam but also is relatively non-volatile and substantially insensitive to exposure to other radiation. The monomers of the invention are generally waxy solids which are represented by the formula:

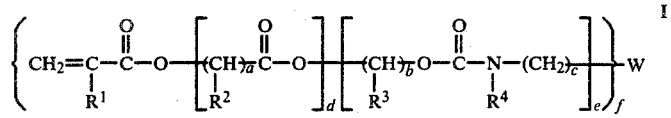

wherein
a=1 or 2
b=2 to 4
c=0 to 1
d=0 or 1 but must be 1 when e=0
e=0 or 1
f=2 or 3
W is divalent or trivalent aliphatic, cycloaliphatic or aromatic hydrocarbyl group of 6–13 carbon atoms;
$R^1$ is hydrogen, methyl or chlorine;
Each $R^2$ and each $R^3$ is independently hydrogen or alkyl of 1 to 4 carbon atoms pendent from an alkylene group, the sum of the carbon atoms in the pendent alkyl groups on one alkylene group being no greater than 4;
Each $R^4$ is independently hydrogen or alkyl of 1-4 carbon atoms.

Compounds represented by Formula I above are available by new combinations of known synthetic processes. The compounds represented by Formula I must all possess acryloxy units and a di- or trivalent hydrocarbyl unit, W.

Depending on whether the values of d is 0 and e is 1 or d is 1 and e is 0 or both are 1, these compounds fall into three classes conveniently referred to as Classes A, B and C. It will be seen that in addition to groups contained by all compounds, the compounds of Class A contain the alkoxycarbonylamidolene units enclosed by brackets "e" of Formula I. Compounds of Class B contain, in addition to the acryloxy and hydrocarbyl units, the acyloxylene units enclosed by brackets "d". Compounds of Class C contain, in addition to the acryloxy and hydrocarbyl units, both acryloxylene units and alkoxycarbonylamidoline units.

The compounds of Class A are thus represented by the formula:

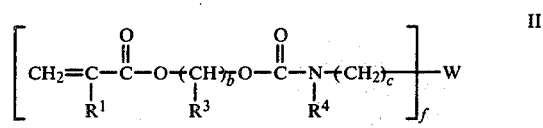

wherein b, c, f, $R^1$, $R^3$, $R^4$ and W are as defined above. Compounds of Class A can be prepared by the reaction, respectively, of 2 or 3 mols of a suitable hydroxyalkyl acrylate with 1 mol of a di- or tri-isocyanate of an aliphatic, cycloaliphatic or aromatic hydrocarbon having 6–13 carbon atoms. Generally the reaction is carried out in an inert solvent such as benzene or toluene at a temperature between about 20° C. and 100° C. for about 10 to 60 minutes. It is preferable that a catalyst for the reaction of isocyanates with alcohols be present, such as, for example, 1–5 mol % of dibutyltin dilaurate, and using 5–25 mol % excess hydroxyalkyl acrylate. The reaction product may then be precipitated from the reaction mixture by dilution with, e.g., hexane, or the reaction solvent is removed by distillation.

Compounds of Class A can also be prepared (and it is preferable to do so when the hydrocarbyl, W, is aliphatic) by reaction of one mol of an aliphatic or cycloaliphatic diamine or triamine with, respectively, two or three mols of an alkylene carbonate, followed, by esterification with two or three mols, respectively, of acrylic, methacrylic or chloroacrylic acid. Alkylene carbonate, in about 5 to 25 mol % excess, is added to the amino compound, in about an equal volume of inert solvent, e.g., benzene, toluene or methanol. Air is excluded, using nitrogen, to avoid the amine's reacting with carbon dioxide in the air. After standing at 20°–50° C. for 3 to 24 hours, the reaction should be complete as shown by absence of amine in the reaction mixture. Solvents are removed by evaporation or distillation. When benzene is used as the reaction solvent the product can usually be collected by filtration of the reaction mixture. The isolated product, a hydroxyalkoxy-carbonamidohydrocarbon, is then converted into its acrylic, methacrylic or chloroacrylic ester using, an acrylate, e.g. methyl or ethyl, and removing alcohol or by reaction, e.g., with acrylyl chloride or anhydride. The reaction is preferably carried out in an inert solvent such as benzene using an esterification catalyst and an inhibitor, e.g. hydroquinone, to avoid polymerization.

Suitable hydroxyalkyl acrylates for use in the preparation of compounds of Class A include 2-hydroxyethyl acrylate, methacrylate and chloroacrylate and the corresponding 3-hydroxypropyl, 4-hydroxybutyl, 2-hydroxypropyl, 3-hydroxybutyl, 2-hydroxy-1,2-dimethylethyl and 2-hydroxy-2-butylethyl esters.

Suitable di- or triisocyanates for use in the preparation of compounds of Class C include 2,4-phenylene diisocyanate, 2,4- and 2,6-tolylene diisocyanate, diphenyl-4,4'-diisocyanate, diphenyl-3,3'-dimethyl-4,4'-diisocyanate, diphenylmethane-4,4'-diisocyanate, 1,5-naphthalene diisocyanate, cumene diisocyanate and aromatic polyisocyanate, e.g. poly(methylenephenylene isocyanates) containing an average of 2 to 2.8 isocyanate groups per molecule. Such poly(methylenephenylene isocyanates) are commercially available under the trade designations "Mondur MRS" from Mobay Co., "Isonate 901" from Upjohn Co., "Papi" from Upjohn Co., etc. Also suitable are aliphatic di- and triisocyanates including 1,6-hexamethylene diisocyanate, 1,8-octamethylene diisocyanate, 1,10-decamethylene diisocyanate and the cycloaliphatic diisocyanates, such as 1,4-cyclohexylene diisocyanates, 4,4'-bis(cyclohexyl)methane diisocyanate, 1,5-tetrahydronaphthylene diisocyanate and 1,3,5-benzene triisocyanate. Lists of many commercially available polyisocyanates are found in Kirk and Othmer, Encyclopedia of Chemical Technology, Vol. 12, 2nd Ed., pp. 46–47, Interscience Publishers (1967).

Suitable amines for use in the preparation of compounds of Class A include aliphatic, cycloaliphatic and aromatic di- or triamines having 6–13 carbon atoms, such as, 1,6-hexamethylene diamine, 1,8-octamethylene diamine, 1,9-nonamethylene diamine, 1,12-dodecamethylene diamine, 1,4-bis(aminomethyl)cyclohexane, 1,4-bis(aminomethyl)benzene, 1,3-diaminocyclohexane and 1,4-diaminocyclohexane; and the corresponding N-lower alkyl substituted diamines such as N,N'-dimethylhexamethylene diamine, dipropylene triamine, 1,7-dimethyldiethylene triamine, 1,3,5-cyclohexane triamine and 1,2,3-triaminomethylpropane.

Suitable alkylene carbonates for use in the preparation of compounds of Class A include ethylene carbonate, propylene carbonate, isopropylene carbonate and the like.

Compounds of Class B are represented by the formula:

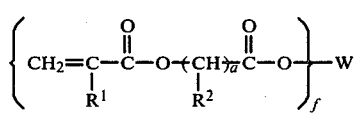

III wherein a, f, R$^1$, R$^2$ and W are as defined above. These compounds can be prepared, for example, by the following steps: An aliphatic or cycloaliphatic diol or triol is first esterified by two or three mols of a halocarboxylic acid and the haloester obtained is then reacted with an acrylic acid in the presence of a base, such as triethyl amine, or an acrylic acid salt such as the sodium, potassium, or triethyl ammonium salt of acrylic, methacrylic or chloroacrylic acid. An alternative procedure is to cause the salt, e.g., of acrylic acid, to react first with the halocarboxylic acid or its lower alkyl ester to form an acryloxycarboxylic acid or ester and then to esterify with the diol or triol.

The esterification step in the preparation of the compounds of Class B can be carried out by first heating, at reflux, a 25–100% by volume mixture of the diol or triol with an excess of halocarboxylic acid in a non-reactive solvent, such as toluene, that codistils with water, and suitably in the presence of 1–2% by weight of an acid catalyst. Heating is continued while removing water of reaction until the reaction is essentially complete. The reaction mixture is cooled, washed with aqueous alkali bicarbonate solution to remove acid, dried and the solvent removed by distillation Alternatively, the esterification may be carried out by ester interchange between a low boiling ester (e.g., methyl or ethyl ester) of the halocarboxylic acid and the diol or triol or by reaction of halocarboxylic acid chloride and the diol or triol. The product is a di- or trihalocarboxylate of the diol or triol.

The ester formed above is then caused to react with a selected acrylic acid by heating for 0.5 to 3 hours at reflux a mixture of the halocarboxylate/ester and an amount, preferably in small stoichiometric excess, of the selected acrylic acid in the presence of a base (e.g. triethyl amine) in about ½ to 2 volumes of an inert solvent such as toluene or dichloroethane. On cooling the mixture, the halide salt is collected and the resulting solution washed with water, dried and the solvent removed by distillation to yield compounds of the invention of Class B.

Suitable diols or triols for use in the preparation of compounds of Class B include aliphatic, cycloaliphatic and aromatic polyols having 6–13 carbon atoms and 2 or 3 primary or secondary hydroxyl groups. Examples of such polyols are 1,6-hexanediol, 1,4-hexanediol, 1,8-octanediol, 1,9-nonanediol, 1,12-dodecanediol, 2-methyl-3,5-hexanediol, 1,4-bis-(hydroxymethyl)cyclohexane, 3-hydroxymethylcyclohexanol, 1,4-bis(hydroxymethyl)benzene, 1,3-cyclohexanediol, 1,4-cyclohexanediol, 1,2,3-trihydroxymethylpropane, 1,3,5-cyclohexanetriol.

Suitable halocarboxylic acids for use in the preparation of compounds of Class B include 2- or 3-halocarboxylic acids having 2–6 carbon atoms such as 2-chloroacetic acid, 2-bromoacetic acid, 2-bromopropionic acid, 3-chloropropionic acid, 3-chlorobutyric acid, 2-bromovaleric acid and 3-chlorohexanoic acid, and the like where halo is Cl or Br. When the preparation of the compounds of Class B utilizes ester interchange, the methyl, ethyl, propyl or butyl esters of the above or other acids can be used.

Compounds of Class C are represented by the formula:

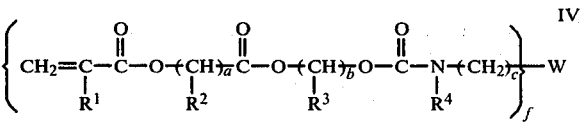

IV wherein a, b, c, f, R$^1$, R$^2$, R$^3$, R$^4$ and W are as defined above. Compounds of Class C can be prepared by first causing a hydroxyalkyl ester of a halocarboxylic acid to react with a di- or triisocyanate of an aliphatic, cycloaliphatic or aromatic hydrocarbon having 6–13 carbon atoms to form a poly(haloacyloxyalkoxycarbonylamido)hydrocarbon by a process such as is used for the reaction of the hydroxyalkyl esters of desired acrylic acids in the preparation of compounds of Class A. The poly(haloacyloxyalkoxycarbonylamido)hydrocarbon can then be caused to react with a desired acrylic acid or salt thereof to yield the compounds of Class C by a process described above for the preparation of compounds of Class B. Other convenient processes for uniting the various units of the compounds of Class C can also be used. Although the order of uniting the various units is of little consequence, it is usually preferable to add the acryloxy unit last because of its tendency to polymerize prematurely.

Suitable hydroxyalkyl esters of halocarboxylic acids for use in the preparation of compounds of Class C are the esters of the halocarboxylic acids suitable for use in the compounds of Class B described previously with any alkylene diol having only primary or secondary hydroxy groups and 2-8 carbon atoms. Suitable diols include ethylene glycol, 1,2- and 1,3-propylene glycol, 1,2-, 1,3-, 1,4- and 2,3-tetramethylene glycol, 2-methylpropylene-1,3-diol, 1,2-, 2,3-, 1,3- and 1,4-pentamethylene glycol, 1,2-dimethylpropylene-1,3-diol, 1,2-, 3,4-, 2,4- and 3,4-hexamethylene glycol and 2,5-octamethylene glycol. The hydroxyalkyl esters can be prepared by direct esterification of halocarboxylic acid and diol or by ester interchange of lower alkyl halocarboxylate and diol. Where it is applicable, it is convenient and preferable to prepare esters by the reaction of halocarboxylic acid and epoxy compound corresponding to the requisite 1,2-diol as described, for example, by C. R. Noller, Chemistry of Organic Compounds, p. 690, W. B. Saunders Co. (1951).

Compounds represented by Formulae III and IV, may be stabilized against polymerization by radiation in the ultraviolet range, but remain susceptible to polymerization by an electron beam, as the result of the peculiar configuration referred to herein as a quasi-ring and illustrated graphically, for the case where a=2, e=0, d=1, f=2 and W=—(CH$_2$)$_6$—:

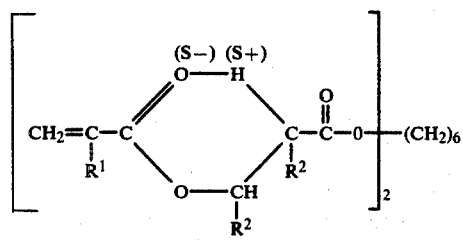

where the (S+) and (S−) provide a bonding force, i.e., intra-dipole-dipole, such that a "quasi-ring" may form.

In these compounds the carboxyl group is an electron-withdrawing group which is incapable of prototropic isomerization. The other alternative groups provided in the above general formula are also of this type. The electron-withdrawing nature of the carboxyl group is believed to permit the intra-dipole-dipole association shown in formula V which dipole association or attraction creates a six membered quasi-ring. When a=1, the resulting dipole-dipole association affords a quasi-ring having five members. The absence of this quasi-ring structure, i.e. Formula II, results in less stabilization of the ethylenic unsaturation attached thereto. Compounds of Formula II are more readily polymerized by U.V. than those of Formulae III or IV.

Examples of electron beam polymerizable monomers include:
Acrylic esteramides of Class A include:
1. 1,4-Bis[2-(acryloxy)ethoxycarbonamidomethyl]cyclohexane
2. 1,4-Bis[2-(methacryloxy)ethoxycarbonamidomethyl]cyclohexane
3. 1,6-Bis[2-(acryloxy)ethoxycarbonamidomethyl]hexane
4. 1,3-Bis[2-(acryloxy)ethoxycarbonamidomethyl]benzene
5. 1,8-Bis[3-(methacryloxy)propoxycarbonamido]octane
6. 2,4-Bis[2-(acryloxy)ethoxycarbonamido]toluene
7. 1,3-Bis[2-(acryloxy)ethoxycarbonamido]benzene
8. 4,4'-Bis[2-(acryloxy)ethoxycarbonamido]diphenylmethane
9. 4,4'-Bis[2-(acryloxy)ethoxycarbonamido]dicyclohexylmethane Activated acrylic compounds of Class B include:
1. 1,6-Bis[2-(acryloxy)acetoxy]hexane
2. 1,6-Bis[2-(acryloxy)propionoxy]benzene
3. 1,12-Bis[2-(acryloxy)acetoxy]dodecane
4. 1,12-Bis[2-(methacryloxy)acetoxy]decane
5. 1,6-Bis[3-(methacryloxy)propionoxy]hexane
6. 1,6-Bis[2-(acryloxy)acetoxy]hexane
7. 1,16-Bis[2-(chloroacryloxy)acetoxy]hexadecane
8. 1,6-Bis[3-(acryloxy)hexoxy]hexane
9. 1,4-Bis[2-(acryloxy)acetoxy]cyclohexane
10. 1,3,5-Tris[2-(acryloxy)acetoxy]cyclohexane
11. Trimethanolpropane triacryloxyacetate
12. 1,6-Bis[3-(acryloxy)-2,3-diethylpropionoxy]hexane Acrylic compounds of Class C include:
1. 1,4-Bis[2-(acryloxyacetoxy)ethoxycarbonamido]benzene
2. 1,6-Bis[4-(acryloxyacetoxy)butoxycarbonamido]hexane
3. 1,6-Bis[2-(acryloxyacetoxy)ethoxy-N-methylcarbonamido]hexane
4. 1,3-Bis[2-(acryloxyacetoxy)ethoxycarbonamido]benzene
5. 1,3-Bis[2-(acryloxyacetoxy)-2,3-diethylethoxycarbonamidomethyl]benzene
6. 1,3-Bis[2-(acryloxyacetoxy)ethoxycarbonamido]cyclohexane
7. 1,3-Bis[2-(acryloxyacetoxy)ethoxy-N-butylcarbonamido]cyclohexane
8. 1,4-Bis[2-(acryloxyacetoxy)ethoxycarbonamidomethyl]benzene
9. 1,3-Bis[2-(3-acryloxypropionoxy)ethoxy-N-methylcarbonamido]cyclohexane
10. 1,3-Bis[2-(3-acryloxybutyryloxy)ethoxycarbonamido]cyclohexane
11. 1,4-Bis[2-(3-methacryloxyhexanoyl)ethoxycarbonamido]cyclohexane
12. 1,4-Bis[2-(3-methacryloxypropionoxy)ethoxy-N-methylcarbonamido]naphthalene
13. 1,3-Bis[2-(acryloxyacetoxy)ethoxy-N-methylcarbonamidomethyl]cyclohexane
14. 1,4-Bis[2-(acryloxyacetoxy)ethoxycarbonamidomethyl]cyclohexane
15. 4,α-Bis[2-(acryloxyacetoxy)ethoxycarbonamido]toluene
16. 1,4-Bis[2-(acryloxyacetoxy)propoxycarbonamidomethyl]cyclohexane
17. Bis{4-[3-(acryloxyacetoxy)propoxycarbonamido]phenyl}methane 18. Bis{4-[2-(acryloxyacetoxy)propoxycarbonamido]cyclohexyl}-methane 19. 2,4-Bis[2-(acryloxyacetoxy)ethoxycarbonamido]toluene Suitable binders for preparation of transfer tapes include alcohol or acetone dispersible thermoplastic, ash-free film-forming resins which are completely volatilized or decomposed to gaseous products at temperatures below about 500° C., and preferably, below about 450° C. The term binders is used to encompass film-forming materials which hold together poorly coherent crystalline monomers which might otherwise fall away in flakes on handling. Examples of such binders include cellulose derivatives such as the hydroxyalkylcelluloses, e.g. hydroxyethylcellulose and hydroxypropylcellulose; the alkoxyalkylcellulases e.g. ethoxyethylcellulose; alkylcelluloses, e.g. ethylcellulose; carboxyalkylcelluloses, e.g., carboxymethylcellulose; polyisobutylenes available under the designation "Vistanex LM-MS" having a molecular weight of about 36,000 to 45,000 from Exon Chemical Co., and polyesters such as polytetramethyleneadipate, Krumbaar K1979 (a polyester available from Krumbaar Chemical Co., a division of Lawter Chemicals, Inc.) and MR85 (an aromatic ketopolyester available from Mohawk Industries, Inc.). The use of a binder is not necessary in all transfer tapes of the invention. Generally, when used, binder is used in an amount 2 to about 15 percent of the total composition. Transfer tapes of the invention consist essentially of 55 to 95, and preferably 65 to 90% by weight filler, 5 to 30% by weight monomer and 0 to 15% by weight binder.

Filler materials for incorporation in transfer tapes are particulate, insulating, resistive, conductive or dielectric materials. The choice is determined by the purpose of the portions to be retained on the substrate. The term dielectric materials will be understood to materials having a high dielectric constant. Generally, the particles have a size of less than about 10 microns and preferably less than 5 microns. Suitable materials include powdered metals for conductors, such as platinum, palladium, silver, gold, gold-platinum, palladium-silver, molybdenum, tungsten; glasses, such as the lead borosilicate glasses, and ceramics, ruthenium oxide, titanium carbide, and others which are used as insulators, dielectrics, resistors or conductors as known in the art.

Glass frit (sometimes also called flux) may be used in conjunction with conductive metals because it fuses and aids in bonding the metal to the substrate. An example of a glass frit material is a borosilicate glass having the approximate composition: $SiO_2$—80%, $B_2O_3$—14%, $Na_2O$—4%, $Al_2O_3$—2%. Other suitable glass frits are compounded from silica and various combinations of oxides of sodium, calcium, barium, magnesium, aluminum, boron, potassium and phosphorous such as described in U.S. Pat. No. 3,726,006.

A transfer composition for use on a transfer tape, and ultimately for transfer to a hybrid circuit substrate, is prepared by milling together the selected monomer, binder and desired filler in a solvent, such as methanol, ethanol, acetone, mixtures of ethanol-acetone, acetone-toluene or the like, to homogeneity using sufficient solvent to provide good coating viscosity. Usually from about 2 to about 10 parts by weight of solvent are used per part by weight of monomer and binder together to give a viscous composition which is somewhat tacky while containing the solvent although the residue may be non-tacky or tackifiable by heating to 20°–150° C.

Transfer tapes are prepared suitably by knife coating the the above viscous composition on a carrier web, preferably having releasing properties, and drying to a relatively non-tacky state. The transfer tape can be rolled up on a core and slit to desired widths as is customary in the tape art. Polyethylene terephthalate is an example of a very satisfactory carrier. Metal foils, such as aluminum or steel foils, and films of polypropylene, polyvinylchloride and the like are also suitable as well as specially treated paper having release coatings to permit easier transfer of the coating. Generally, the carriers are from about 10 to 100 microns in thickness and are coated with the above composition at a wet thickness of about 25 to 100 microns. Dried thickness of the coating is generally from about 10 to 75 microns but may be greater or less if desired.

The tapes are used in preparing hybrid circuits by applying the transfer tape to a heated alumina substrate (usually 94–99.9% alumina or high purity beryllia), cooling the assembly and then peeling away the carrier backing. The transferred composition, which is now on the surface of the alumina substrate and is often herein referred to as a "transfer", is exposed to an electron beam through a suitable mask to form an image. The mask is prepared by etching metal from metal coated carrier. A suitable carrier is about 15 microns thick polyamide film with a copper layer about 25 microns thick. Etching is effected in, e.g., ferric chloride solution after applying photo-resists by standard printed circuit methods. Exposure to an electron beam may be made in vacuum or in air. The voltage of the electron beam may be adjusted (raised or lowered) to penetrate the transfer thickness and thus to insure complete polymerization throughout the thickness of the transfer. This voltage can vary from about 5 kV to 300 kV or higher depending upon the mask, the transfer thickness and loading content of the particular filled transfer as well as whether exposure is in air or vacuum. An exposure current density of from $10^8$ to $10^{12}$ electrons per square centimeter can be used to expose the transfer.

The exposure may also be made without a mask using raster scanning techniques well known in the television and electron-beam recording industries.

After exposure, a recirculating solvent spray developer system is conveniently used to dissolve away all unpolymerized material and suspend the filler associated therewith and leave the image exposed by the electron beam. A collection filter in the recirculating developer system can be used to collect all of the suspending particulate material. This recovered material can then be recycled. Ethanol-acetone in 1:1 proportions provides a convenient fluid for use in this system.

The substrate and the image are freed from residual solvent, heated to volatilize polymer and binder and fired to maturity in a furnace at a temperature to effect sintering of the image particles as would be done in a standard thick film fixing process. After firing, permanent pattern remains on the substrate.

Further layers of dielectric, conductor or resistors can be added as desired by applying tapes filled with the desired material, exposing and developing away the unwanted material, drying and firing as above. It is only necessary to avoid firing at higher temperatures than were used for previous applied patterns.

The invention is now further illustrated by examples in which parts are by weight unless otherwise specified and temperatures are in °C.

EXAMPLE 1

In a 250 ml 2-neck flask fitted with thermometer, magnetic stirrer and Dean-starke trap, are placed 29.5 g. (0.25 mol) of 1,6-hexanediol, 50.1 g. (0.53 mol) of chloroacetic acid, 1.9 g. (0.01 mol) of p-toluenesulfonic acid monohydrate and 60 ml of toluene. The reactants are heated for about 1 hour, during which time about 9 g. of water are collected in the trap. The reaction mixture is cooled, and washed successively with water, 50 ml of 10% solution bicarbonate solution and again with water. The toluene mixture is dried over anhydrous sodium sulfate, filtered and then evaporated under reduced pressure to give a residue of 1,6-hexanediol bis(2-chloroacetate).

A 500 ml flask is charged with 54.2 g. (0.20 mol) of the above bis(chloroacetate), 30.25 g. (0.42 mol) acrylic acid, 20.2 g. (0.2 mol) triethylamine and 100 mol of dichloroethane and refluxed for about one hour. The reaction mixture is allowed to cool to room temperature and filtered. The filtrate is washed with water three times and dried over anhydrous sodium sulfate. Solvent and other volatile matter are removed under reduced pressure to yield 1,6-bis[2-(acryloxy)acetoxy]hexane melting point 66° C. It showed infra red maxima at 5.65, 5.73, 6.07, 6.14 and 6.99μ.

EXAMPLE 2

The procedure of Example 1 is repeated using 50.5 g. (0.25 mol) of 1,12-decanediol in place of the hexanediol. A waxy product 1,12-bis[2-(acryloxy)acetoxy]dodecane is obtained melting about 72° C.

EXAMPLE 3

A 250 ml. 2-neck flask fitted with a magnetic stirrer and a gas bubbling device is charged with 35.5 g. (0.25 mol) of 1,4-bis(aminomethyl)cyclohexane, 46.65 g. (0.53 mol) of ethylene carbonate and 75 ml of benzene. The flask is flushed with $N_2$ for about 3 minutes and closed. The reaction mixture is stirred for about 10 hours at room-temperature under the $N_2$ atmosphere. The precipitate is collected and washed with benzene and dried at 100° C. and 0.2 mm Hg pressure to give 1,4-bis(hydroxyethoxycarbonamidomethyl)cyclohexane.

A solution of 47.7 g. (0.15 mol) of the above cyclohexane compound, 30.25 g. (0.32 mol) of chloroacetic acid, 1.3 g. (0.008 mol) of p-toluenesulfonic acid in 130 ml of toluene is refluxed for about 5 hours while separating about 5.4 g. (0.3 mol) of water. The reaction mixture is cooled to room temperature, washed successively with water, 250 ml of a 10% sodium bicarbonate solution, and again with water and the toluene solution stripped of volatiles under reduced pressure to give 1,4-bis(chloroacetoxyethoxycarbonamidomethyl)cyclohexane.

A solution of 47.1 g. (0.1 mol) of the above chloroacetoxy compound, 9.4 g. (0.13 mol) of acrylic acid, 11.1 g. (0.11 mol) of triethylamine and 100 ml. of dichloroethane is refluxed for about one hour, cooled to room-temperature and filtered. The filtrate is washed with water three times and dried over anhydrous sodium sulfate. The volatile solvents are removed under reduced pressure. The white residue is 1,4-bis[2-(acryloxyacetoxy)ethoxycarbonamidomethyl]cyclohexane, m.p. 104°–106° C. Infra red maxima are at 3.00, 5.65, 5.73, 6.07, 6.57 and 7.17μ.

EXAMPLE 4

The procedure of Example 3 is repeated employing 34.0 g. (0.25 mol) m-xylylene diamine and 46.6 g. (0.53 mol) ethylene carbonate in place of the bis(aminomethyl)cyclohexane and ethylene carbonate in the first step. The resulting 1,3-bis[2-(acryloxyacetoxy)ethoxycarbonamido]benzene is a slightly colored waxy solid melting 67°–70° C. Infra red maxima are at 2.92, 3.00, 5.66, 5.79, 6.06, 6.20, 6.55, 7.00, 11.28, 12.85 and 14.22μ.

EXAMPLE 5

A. In a 250 ml flask is prepared a solution of 28.35 g. (0.3 mol) of chloroacetic acid in 40 ml. of anhydrous benzene and to it are added 18.0 g. (0.31 mols) of propylene oxide in 10 ml of anhydrous benzene and the mixture refluxed for 10 minutes. The solution is added over five minutes to a warm (70° C.) and stirred solution of 35.0 g. (0.14 mol) of bis-(4-isocyanatophenyl)methane in 50 ml of anhydrous benzene containing about 2.0 g. (0.003 mol) of dibutyltin dilaurate. Reaction is completed by refluxing for 20 minutes. The mixture is cooled and precipitated by addition of about 50 ml of petroleum ether. The precipitate is collected and washed with 50 ml of a 1 to 1 mixture of benzene and petroleum ether. It is then added to 21.6 g. (0.3 mol) of acrylic acid and 28.3 g. (0.28 mol) of methylamine in 100 ml of dichloroethane and refluxed for one hour. The reaction mixture is cooled to room temperature and filtered. The filtrate is washed with water three times and dried over anhydrous sodium sulfate. The solution is separated and the volatiles evaporated under reduced pressure. Bis{4[2-(acryloxyacetoxy)isopropoxycarbonamido]-phenyl}methane is obtained as a whitish solid m.p. 71°–74°. Infra red absorption maxima are at 2.93, 5.66, 5.77, 6.07, 6.18, 6.25, 6.54, 7.00 and 12.31μ.

B. The above procedure is repeated using 23.5 g. (0.14 mol) 1,6-hexane diisocyanate and 13.7 g. (0.31 mol) ethylene oxide in place of the diisocyanate and propylene oxide used above. 1,6-Bis[2-(acryloxyacetoxy)-ethoxy carbonamido]hexane is obtained as a waxy solid, m.p. 124°–7° C. IR 2.94, 5.65, 5.73, 6.10, 6.20 and 6.55μ.

EXAMPLE 6

The procedure of Example 5 is repeated using 36.7 g. (0.14 mol) of 4,4'-methylene bis(cyclohexyl isocyanate) in place of the diphenyl methane isocyanate used there. The product is obtained as a whitish solid m.p. 121° to 124° C. Infra red absorption maxima are at 2.98, 5.50, 5.78, 6.09, 6.16, 6.77, 6.90 and 7.12μ.

EXAMPLE 7

The procedure of Example 5 is again repeated except that 24.4 g. (0.14 mol) toluylene 2,4-diisocyanate and 13.7 g. (0.31 mol) ethylene oxide are used for the isocyanate and propylene oxide reactants of that example. 2,4-Bis[2-(acryloxyacetoxy)ethoxycarbonamido]toluene is obtained as a waxy solid m.p. 72° to 74° C. Infra red absorption maxima are at 2.92, 2.99, 5.75, 5.85, 6.08, 6.18, 6.25, 7.02, 11.35 and 12.34μ.

EXAMPLE 8

In a 750 ml 3-neck flask fitted with thermometer, reflux condenser magnetic stirrer and dropping funnel are placed 50.0 g. (0.2 mol) of diphenylmethane 4,4'-diisocyanate, 2.5 g. (0.004 mol) of di-butyltin dilaurate and 60 ml. of benzene. The mixture is stirred and heated to 70° C. on a steambath. Heating is discontinued and a solution of 48.7 g. (0.42 mol) of hydroxy-ethyl acrylate in 20 ml of benzene is added slowly at a rate which maintains the temperature of the reaction mixture at about 70°–75° C. (about 10 minutes). The mixture is refluxed for a further 20 minutes, cooled to room temperature and precipitated by adding 50 ml of petroleum ether. The precipitate is collected, washed with 1:1 (volume) benzene-petroleum ether and freed from volatiles at reduced pressure. 4,4'-Bis[2-(acryloxy)ethoxycarbonamido]diphenyl methane is obtained as a whitish solid; m.p. 76°–78°. Infra red absorption maxima are 2.90, 3.00, 5.79, 6.03, 6.18, 6.23, 6.56, 7.00 and 12.35μ.

EXAMPLE 9

The procedure of Example 8 is repeated using 4,4'-methylene bis(cyclohexyl isocyanate) in the same molar proportion in place of the diisocyanate used there. The product is 4,4'-bis[2-(acryloxy)ethoxycarbonamido]-dicyclohexyl methane obtained as a white solid m.p. 126° to 129° C. Infra red absorption maxima are at 2.98, 5.46, 5.80, 6.10, 6.16 and 7.14μ.

EXAMPLE 10

The procedure of Example 8 is repeated using toluylene 2,4-diisocyanate and 2,4-bis[2-(acryloxy)ethoxycarbonamido]toluene is obtained m.p. 75° to 77° C. Infra red absorption maxima are at 2.93, 3.00, 5.83, 6.12, 6.19, 6.25, 7.02, 11.33 and 12.32μ.

EXAMPLE 11

An electron beam sensitive transfer tape is prepared by heating 1 part by weight of hyroxypropyl cellulose in 15 parts by weight ethanol until solution occurs and then dissolving 3 parts by weight of 1,4-bis[2-(acryloxyacetoxy)ethoxycarbonamidomethyl]cyclohexane:

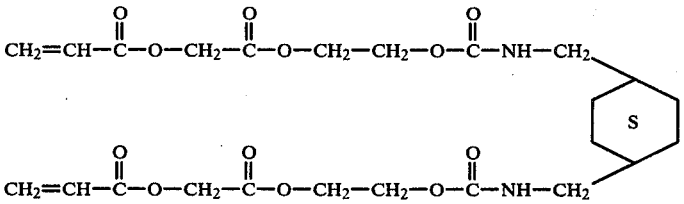

as obtained in Example 3. To this solution are added 25 parts by weight (86.3%) of silver-palladium powder (1.5 micron; available from Cernonics, Inc.) and containing 87% silver, 5% palladium and 8% glass frit and the mixture is ball milled for about one-half hour. The resulting dispersion is knife-coated on 15 micron polyester carrier film at a coating thickness of 75 microns and the coated film dried at room temperature. The dry coating thickness is 20 microns. The coated film is slit into strips about 2.5 cm wide. The coated layer (transfer layer) is nontacky and the strips can be rolled tightly on themselves and readily unrolled.

The tape is applied to a 96% alumina substrate by heating the substrate on a hot plate to about 75° C. and a portion of the strip prepared above is placed on the heated substrate, coated surface down, and pressed into intimate contact with the substrate using a small roller. The assembly is then removed from the hot plate and cooled to room temperature and the carrier film is stripped away rapidly leaving the transfer layer firmly attached to the substrate. The assembly is then covered with a metal stencil (copper 25 microns thick on a 15 micron thick substrate of polyimide film) of a circuit pattern and exposed to an electron beam for one second. The beam floods a 25 cm square area at a distance of about 20 mm. from the Leonard window of the electron source operating at 105 kV and 2 ma. (Similar results are obtained with exposures of about 0.5 second at 125 kV and 2 ma.) The exposed substrate is developed by spraying with 1:5 acetone:ethyl alcohol (volume/volume) to remove unreacted composition in unexposed areas and leaving polymerized composition in the exposed areas. The imaged substrate is fired in a furnace with a 40 minute cycle profiled for 10 minutes at a peak temperature of 850° C. to produce a substrate bearing precise conductive circuitry having line widths as small as 75 microns. Repetition of these operations produces substrates bearing essentially identical conductive circuitry.

EXAMPLE 12

A substrate bearing tungsten circuitry is prepared by the process described in Example 11 except that, in place of the silver-palladium powder, a 1.5 powder of 95% tungsten and 5% glass frit is used and it is applied, to an unfired "green" 95% alumina substrate (prepared as described in U.S. Pat. No. 2,966,719) and the image green substrate is then fired for 20 hours at 1650° C. A cured substrate bearing a tungsten conductive pattern is obtained. Repetition of the operation produces substrates bearing essentially identical conductive patterns.

EXAMPLE 13

An electron beam sensitive transfer tape suitable for the preparation of insulating patterns on substrates was prepared as follows:

A solution is prepared in 20 g. of ethanol from 0.75 g. of aromatic ketopolyester available as MR85, 0.75 g. hydroxypropyl cellulose and 4.0 g. of 2,4-bis[2-(acryloxyacetoxy)ethoxycarbonamido]toluene (m.p. 73°–76° C.) produced in Example 7 by stirring and heating. To the solution is added 14.0 g. (65.1%) of a lead alumina silicate glass frit (available from American Porcelain Company and having the composition: PbO—32%, SiO$_2$—30%, Al$_2$O$_3$—11%, ZnO$_2$—10%, TiO$_2$—9% and BaO—8%). The mixture is ball mixed for about one hour using about 12 mm i.a. alumina ceramic balls.

The composition is knife-coated onto polyester film as in Example 11, dried and slit into 2.5 cm. wide strips of tape. The tape is non-tacky and can be rolled tightly and readily unrolled without flaking or cracking. The coated composition is transferred to an alumina substrate at a temperature of 120° C., the coated substrate exposed to an electron beam image, developed with a spray of 5 parts alcohol to 1 part acetone, and fired as in Example 11. An insulating pattern that is tightly bonded to the substrate and has a resolution of at least 75 microns is obtained. Repetition of these operations produces substrates bearing essentially identical insulating patterns with very little deviation in quality.

EXAMPLE 14

The procedure of Example 13 is repeated using the components:

|  | Parts by Weight | Weight Percent |
|---|---|---|
| Ethanol | 20.0 |  |
| Ethyl Cellulose | 2.3 | 11 |
| Monomer* | 4.6 | 22 |
| Glass Frit (as above) | 14.0 | 67 |

*1,3-Bis[2-acryloxyacetoxy)ethoxycarbonamidomethyl]benzene; m.p. 67°-70° C. (from Example 4).

The composition is transferred from the tape to a substrate at 120° C. Electron beam produced images are developed and fired as in Example 13. Insulating images obtained have a resolution of about 250 microns width. Repetition of these operations produces substrates bearing essentially identical insulating patterns.

EXAMPLE 15

The procedure of Example 13 is repeated using the components:

|  | Parts by Weight | Weight Percent |
|---|---|---|
| Ethanol | 20 |  |
| MR85 | 0.75 |  |
| Binder- |  | 5.9 |
| Hydroxypropyl cellulose | 0.75 |  |
| Monomer* | 4.0 | 15.7 |
| Glass Frit | 20.0 | 78.4 |

*Same as Example 11.

The composition is transferred from the tape to a substrate at 120° C. Fired, electron-beam-produced, insulating images have a resolution of at least 250 microns.

EXAMPLE 16

The procedure of Example 13 is repeated using the components:

|  | Parts by Weight | Weight Percent |
|---|---|---|
| Ethanol | 20 |  |
| MR85 | 0.75 |  |
| Binder- |  | 7.0 |
| Hydroxypropyl cellulose | 0.85 |  |
| Monomer* | 6.0 | 27.9 |
| Filler - Glass Frit | 14.0 | 65.1 |

*1,6-Bis[2-(arcyloxyacetoxy)ethoxy carbonamido]hexane, m.p. 78°-80° C. (from example 5B).

The composition provides flexible tapes, the transfer layer of which can be transferred to substrates at 120° C. Fired images have resolutions of at least 125 microns width. Repetition of these operations produces substrates bearing essentially identical dielectric patterns.

What is claimed is:

1. A monomer polymerizable under the influence of electron-beam represented by the structure

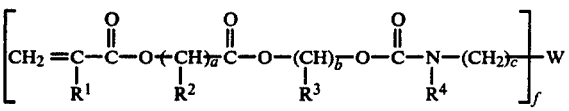

wherein a=1 or 2, b=2 to 4, c=0 or 1, f=2 or 3;

W is divalent or trivalent aliphatic, cycloaliphatic or aromatic hydrocarbyl group of 6–13 carbon atoms;

$R^1$ is H, $CH_3$ or Cl;

Each $R^2$ and each $R^3$ is independently H or alkyl of 1 to 4 carbon atoms pendent from an alkylene group, the sum of the carbon atoms in the pendent alkyl groups on one alkylene group being no greater than 4 and Each $R^4$ is independently H or alkyl of 1 to 4 carbon atoms.

2. 1,4-Bis-[2-(acryloxyacetoxy)ethoxycarbonamidomethyl]cyclohexane.

3. 1,3-Bis-[2-(acryloxyacetoxy)ethoxycarbonamidomethyl]benzene.

4. 4,4'-Bis-(2-acryloxyethoxycarbonamido)diphenylmethane.

* * * * *